(12) United States Patent
Schwab et al.

(10) Patent No.: US 8,764,832 B2
(45) Date of Patent: Jul. 1, 2014

(54) ANTERIOR HYBRID IMPLANT

(75) Inventors: Frank J. Schwab, New York, NY (US); Anthony J. Melkent, Memphis, TN (US); Brian Robert Thoren, Memphis, TN (US)

(73) Assignee: Warsaw Orhtopedic, Inc., Warsaw, IN (US)

( * ) Notice: Subject to any disclaimer, the term of this patent is extended or adjusted under 35 U.S.C. 154(b) by 1964 days.

(21) Appl. No.: 11/527,123

(22) Filed: Sep. 26, 2006

(65) Prior Publication Data

US 2007/0233248 A1    Oct. 4, 2007

Related U.S. Application Data

(60) Provisional application No. 60/720,555, filed on Sep. 26, 2005.

(51) Int. Cl.
*A61F 2/44* (2006.01)
*A61F 2/30* (2006.01)

(52) U.S. Cl.
CPC ..... *A61F 2/4465* (2013.01); *A61F 2002/30841* (2013.01); *A61F 2310/00023* (2013.01)
USPC ...................................................... 623/17.16

(58) Field of Classification Search
CPC ............ A61F 2/446; A61F 2002/4475; A61F 2002/30115; A61F 2/30767; A61F 2250/0018; A61F 2002/0081; A61F 2310/00023
USPC ...................................................... 623/17.16
See application file for complete search history.

(56) References Cited

U.S. PATENT DOCUMENTS

| | | | |
|---|---|---|---|
| 5,071,437 A | 12/1991 | Steffee | |
| 5,192,327 A | 3/1993 | Brantigan | |
| 5,397,364 A | 3/1995 | Kozak et al. | |
| 6,039,762 A | 3/2000 | McKay | |
| 6,126,688 A | 10/2000 | McDonnell | |
| 6,159,211 A | 12/2000 | Boriani et al. | |
| 6,241,733 B1 | 6/2001 | Nicholson et al. | |
| 6,296,665 B1 | 10/2001 | Strnad et al. | |
| 6,447,543 B1 * | 9/2002 | Studer et al. | 623/17.11 |
| 6,461,359 B1 | 10/2002 | Tribus et al. | |
| 6,626,943 B2 | 9/2003 | Eberlein et al. | |
| 6,645,248 B2 | 11/2003 | Casutt | |
| 6,679,887 B2 | 1/2004 | Nicholson et al. | |
| 6,712,852 B1 | 3/2004 | Chung et al. | |
| 6,790,233 B2 | 9/2004 | Brodke et al. | |
| 7,137,997 B2 * | 11/2006 | Paul | 623/17.11 |
| 7,662,186 B2 * | 2/2010 | Bagga et al. | 623/17.16 |
| 2002/0169508 A1 * | 11/2002 | Songer et al. | 623/17.11 |
| 2003/0040799 A1 * | 2/2003 | Boyd et al. | 623/17.11 |
| 2003/0105527 A1 | 6/2003 | Bresina | |
| 2003/0109928 A1 | 6/2003 | Pasquet et al. | |

(Continued)

FOREIGN PATENT DOCUMENTS

| | | |
|---|---|---|
| EP | 1 088 533 A1 | 4/2001 |
| WO | WO 00/16711 A2 | 3/2000 |

(Continued)

*Primary Examiner* — Ellen C Hammond

(57) ABSTRACT

An implant configured for placement through an anterior surgical approach made of at least two different materials. The implant may include materials with varying radiolucency and mechanical properties. Such a hybrid implant may offer controlled radiographic visibility and optimized structural properties for implant placement, including placement for use in spinal arthrodesis.

30 Claims, 12 Drawing Sheets

(56) References Cited

U.S. PATENT DOCUMENTS

| | | |
|---|---|---|
| 2003/0125739 A1 | 7/2003 | Bagga et al. |
| 2003/0139812 A1 | 7/2003 | Garcia et al. |
| 2003/0187506 A1* | 10/2003 | Ross et al. ................ 623/17.13 |
| 2004/0034430 A1 | 2/2004 | Falahee |
| 2004/0064184 A1 | 4/2004 | Chung et al. |
| 2004/0068318 A1 | 4/2004 | Coates et al. |
| 2004/0073314 A1* | 4/2004 | White et al. ............... 623/17.15 |
| 2004/0082999 A1 | 4/2004 | Mathys, Jr. et al. |
| 2004/0122518 A1 | 6/2004 | Rhoda |
| 2004/0126407 A1 | 7/2004 | Falahee |
| 2004/0158324 A1 | 8/2004 | Lange |
| 2005/0027360 A1 | 2/2005 | Webb et al. |
| 2005/0049706 A1* | 3/2005 | Brodke et al. ............. 623/17.11 |
| 2005/0096745 A1 | 5/2005 | Andre et al. |
| 2005/0143822 A1 | 6/2005 | Paul |
| 2005/0177238 A1 | 8/2005 | Khandkar et al. |
| 2005/0187625 A1* | 8/2005 | Wolek et al. ............... 623/17.11 |
| 2005/0251260 A1 | 11/2005 | Gerber et al. |
| 2006/0100705 A1* | 5/2006 | Puno et al. ................. 623/17.11 |
| 2008/0262623 A1* | 10/2008 | Bagga et al. ............... 623/17.16 |

FOREIGN PATENT DOCUMENTS

| | | |
|---|---|---|
| WO | WO 02/080823 A1 | 10/2002 |
| WO | WO 03/068111 A1 | 8/2003 |
| WO | WO 2004/071346 | 8/2004 |

* cited by examiner

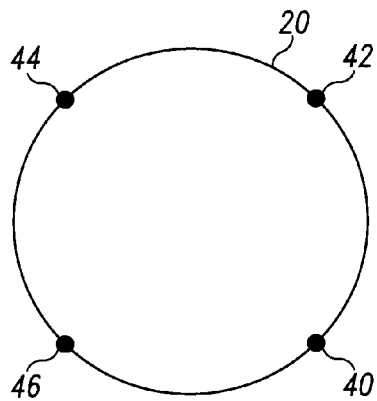
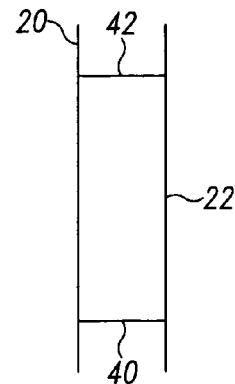
Fig. 21A  Fig. 21B
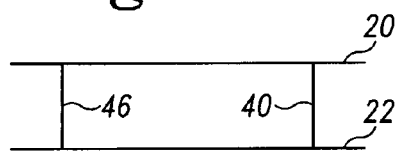
Fig. 21C
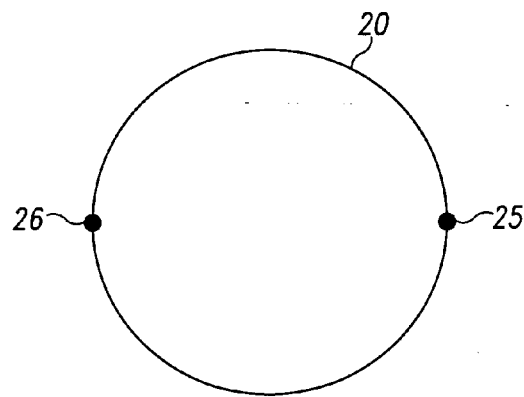
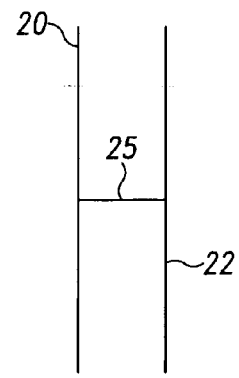
Fig. 22A  Fig. 22B
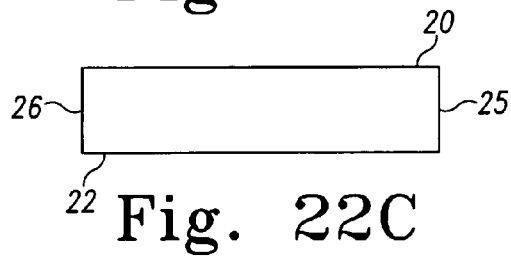
Fig. 22C

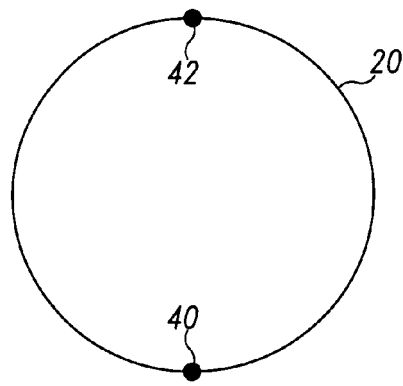
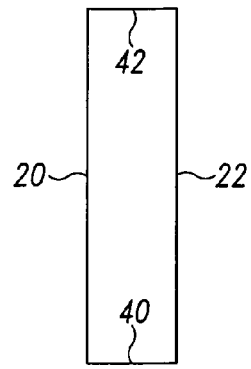
Fig. 23A        Fig. 23B
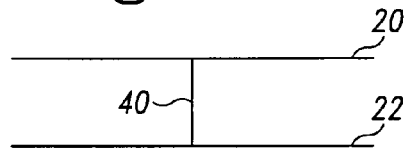
Fig. 23C
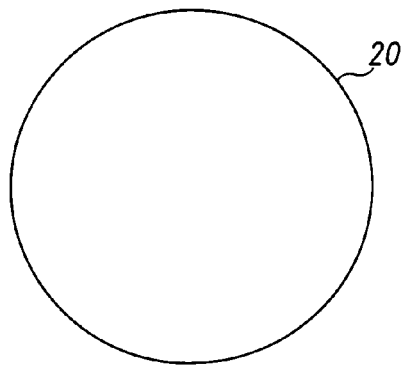
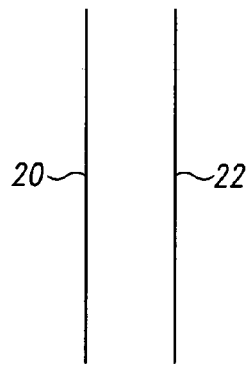
Fig. 24A        Fig. 24B
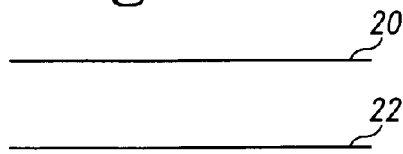
Fig. 24C

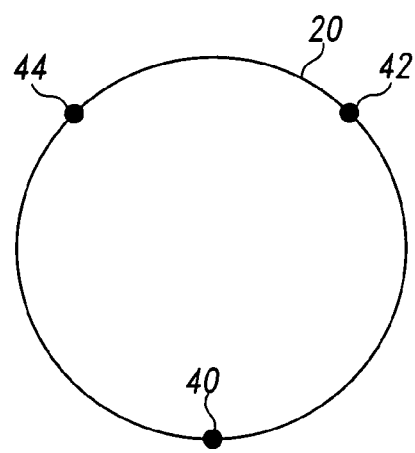
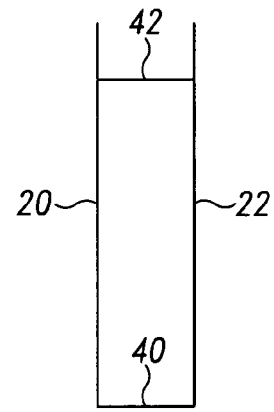
Fig. 25A  Fig. 25B
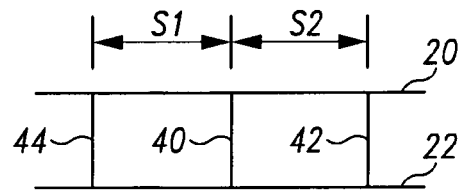
Fig. 25C

ANTERIOR HYBRID IMPLANT

CROSS REFERENCE

This application claims priority from U.S. Provisional Patent Application Ser. No. 60/720,555, filed on Sep. 26, 2005, entitled "Hybrid Intervertebral Spinal Fusion Implant." The following applications also claim priority to the above referenced provisional application and are related to the present application. They are incorporated by reference herein:

U.S. Utility patent application Ser. No. 11/527,121 filed on Sep. 26, 2006 and entitled "Transforaminal Hybrid Implant;" and U.S. Utility patent application Ser. No. 11/527,122 filed on Sep. 26, 2006 and entitled "Hybrid Intervertebral Spinal Fusion Implant."

TECHNICAL FIELD

The present invention relates generally to the field of medical implants and methods, and more specifically to interbody spinal implants which may be adapted for placement into an implantation space created across the height of a disc space between two adjacent vertebral bodies for the purpose of correcting disease, dysfunction, or degeneration at that interspace, and any related methods. The spinal implants may be made of a plurality of implant materials, which bear differing degrees of radiographic lucency. These materials may include bone and may or may not be resorbable. The implants of some embodiments are adapted such that radiographic visualization of operative placement and eventual bone healing can be observed.

BACKGROUND

Implants for placement in the intervertebral space between adjacent vertebral bodies in the spine come in a wide range of shapes and sizes. These implants are usually made entirely of one material, although the type of material can vary significantly between specific implants. Such implants for use in human spinal surgery include implants made entirely of metals, such as titanium or stainless steel, or synthetic radiolucent materials such as carbon-carbon composites or poly-ether-ether-ketone (PEEK). Implants may have a structure designed to promote fusion across adjacent vertebral bodies by allowing bone to grow through and around the implant. The operative placement of intervertebral implants is optimized by radiographic opacity. However, a relatively radiolucent implant material optimizes postoperative evaluation of bone growth and fusion across an intervertebral space. While these implants may contain marking beads or radio opaque markers they do not structurally benefit from radio opaque materials. In some configurations, metals, some of which are opaque on radiographs, provide greater strength and resistance to impaction during implantation. Metallic implants may offer reduced wall thickness of structural components and offer increased volume for bone graft and other agents within an implant.

As it is desirable to take advantage of benefits of radiolucent and radio-opaque materials in an implant, there exists a need for an improved implant made of different structural materials with different properties of radiographic appearance. For some implants, it is desirable to provide optimization of mechanical properties, while permitting generous bone filling and bone through-growth. These characteristics may be applied in some embodiments in combination with an ability to radiographically determine bone-implant interaction and bone growth into and around the implant.

SUMMARY

Embodiments of the invention may include an artificial interbody spinal fusion implant made of structural materials with varying radiolucency and mechanical characteristics. Implants may be provided for insertion at least in part into an implantation space formed across the height of a disc space between adjacent vertebral bodies of a human spine. The implant of some embodiments consists of at least two radiographically distinct imaging materials: a radiolucent portion, and a radio-opaque portion. The radio-opaque materials of some embodiments are arranged toward the vertebral endplates with minimal obstruction to radiographic visualization through the implant from anterior to posterior and/or from lateral directions. Embodiments of the implant may include upper and lower portions adapted to be placed within the intervertebral space to contact and support the adjacent vertebral bodies. Upper and lower portions of the implant may include at least one opening in communication with one another and adapted to hold bone growth promoting material and/or bone graft for permitting the growth of bone from vertebral body to vertebral body through the implant. Embodiments of the invention include an artificial interbody spinal implant containing at least two different materials for insertion at least in part into an implantation space formed across the height of a disc space between adjacent vertebral bodies of a spine. Implant embodiments may employ materials that bear a structural role in the design of the implant, and at least a portion of a leading end of the implant may have a reduced height to facilitate insertion of said implant between the two adjacent vertebral bodies. Implants may have a maximum length less than and approximating the posterior to anterior or right to left length of the vertebral bodies. Some embodiments also include a bone engaging surface formed on the exterior of at least the upper and lower portions for engaging the adjacent vertebral bodies, such as one or more protrusions, ratchets, spikes, roughened surfaces or knurling. Embodiments of the implant may be combined with a bone growth or bone healing promoting material such as, but not limited to, bone, bone derived products, demineralized bone matrix, mineralizing proteins, ossifying proteins, bone forming cell differentiating substance, bone morphogenetic protein, hydroxyapatite, and gene therapy material leading to the production of bone. Embodiments of the implant may also be combined with a therapeutic substance for the treatment of infection, tumor or other pathologic process. In some embodiments of the invention, one component material is relatively, or absolutely radiolucent. In some embodiments of the invention, one component material is radio-opaque. One component material of the implant may be at least in part resorbable. In some embodiments, at least a portion of an implant is treated to promote bone in-growth between the implant and adjacent vertebral bodies. Embodiments of the implant may be used in combination with at least one spinal fixation implant. Embodiments of the implant may include a hollow interior and at least one area for attachment or interaction with an insertion device for surgical placement or removal from the intervertebral space. Upper and lower surfaces of some embodiments of the implant may include a plurality of openings. Embodiments of the implant may be designed to be inserted adjacent to a second implant into a disc space between adjacent vertebral bodies, the second implant being of identical or differing shape. At least one opening may be between the leading and trailing ends of embodiments of the implant. Upper and lower portions or surfaces of embodiments of the implant may be at least in part generally parallel to one another or may be configured with an angular relationship to each other for allowing angulation of adjacent vertebral bodies relative to each other.

Another embodiment of the invention is an intervertebral implant having a generally rounded exterior shape for promoting fusion between an inferior vertebral body and a superior vertebral body. The embodiment includes a first rim around a periphery of the implant, the first rim having a detectable radiographic signature, and a member coupled to the first rim. The member has less of a radiographic signature than the first rim, and the member adds vertebral spacing height to the first rim.

Yet another embodiment of the invention is a method of implanting an intervertebral implant from an anterior surgical approach. The method includes providing an implant comprising: a first rim around a periphery of the implant, the first rim having a detectable radiographic signature, and a member coupled to the first rim. The member having less of a radiographic signature than the first rim, and the member adds vertebral spacing height to the first rim. The method further includes radiographically observing placement of the implant between superior and inferior vertebral bodies by way of one or more of an anterior to posterior radiographic view and a lateral radiographic view. The method also may include radiographically observing bone growth between the superior and inferior vertebral bodies by way of one or more of an anterior to posterior radiographic view and a lateral radiographic view.

Still another embodiment of the invention is a method of assembling an intervertebral implant. A implant is provided for the method comprising: a first rim around a periphery of the implant, the first rim having a detectable radiographic signature, a support coupled to the first rim, the support having a detectable radiographic signature, and a second rim coupled to the support, the second rim having a detectable radiographic signature. The method further includes applying a member between the first rim and the second rim, the member having less of a radiographic signature than the first rim.

BRIEF DESCRIPTION OF THE DRAWINGS

FIGS. 21A, 21B, and 21C are plan (axial), side (lateral), and posterior views respectively of components of an embodiment of the invention.

FIGS. 22A, 22B, and 22C are plan (axial), side (lateral), and posterior views respectively of components of an embodiment of the invention.

FIGS. 23A, 23B, and 23C are plan (axial), side (lateral), and posterior views respectively of components of an embodiment of the invention.

FIGS. 24A, 24B, and 24C are plan (axial), side (lateral), and posterior views respectively of components of an embodiment of the invention.

FIGS. 25A, 25B, and 25C are plan (axial), side (lateral), and posterior views respectively of components of an embodiment of the invention.

DETAILED DESCRIPTION

The following description is intended to be representative only and not limiting and many variations can be anticipated according to these teachings, which are included within the scope of this inventive teaching. Reference will now be made in detail to embodiments of this invention, examples of which are illustrated in the accompanying drawings. Wherever possible, the same reference numbers will be used throughout the drawings to refer to the same or like parts.

Figure 1:
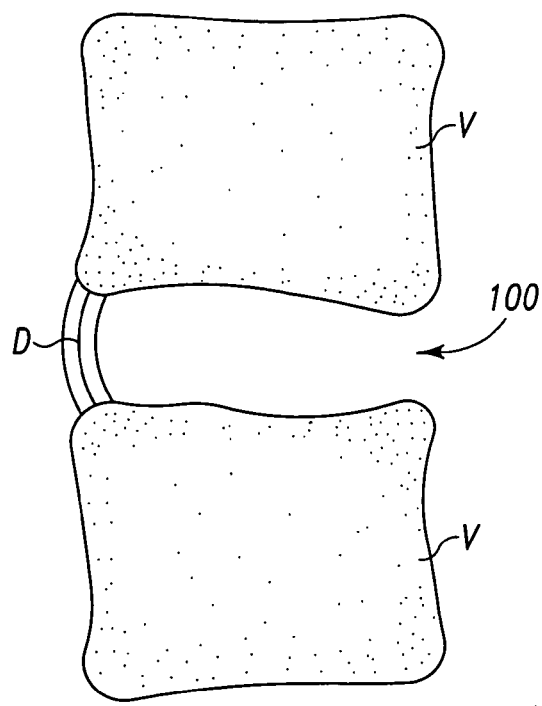
FIG. 1 is a side view of two adjacent vertebral bodies in a lumbar spine with an implantation space formed across the height of the spinal disc space.
Figure 2:
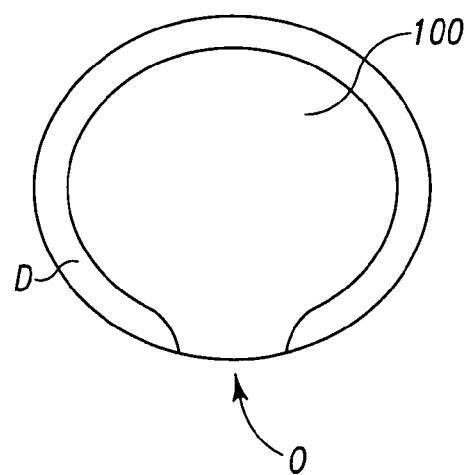
FIG. 2 is a top plan view of a vertebral body in a lumbar spine with an implantation space formed through a posterior approach.
Figure 3:
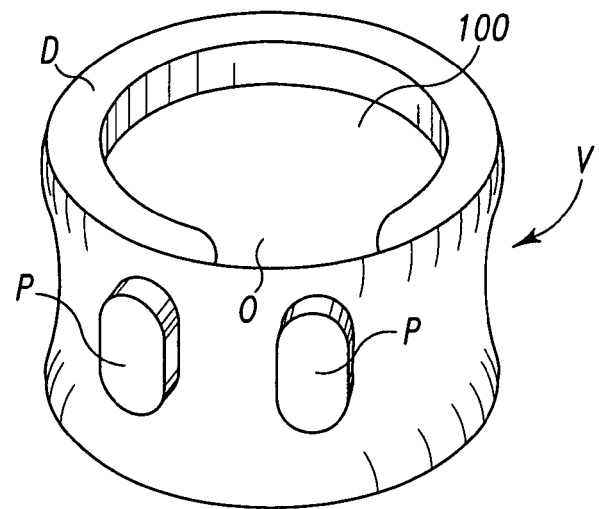
FIG. 3 is a side perspective view of the implantation space of FIG. 2.

FIGS. 1-3 show an implantation space 100 formed across the height of a spinal disc D between vertebral bodies V in the lumbar spine. In other embodiments, the vertebral bodies may be bodies of the cervical or thoracic spine as well. It is understood that numerous methods exist and that any method and instrumentation designed for the purpose may be applied to prepare the desired implantation space and perform disc and soft tissue removal in such a manner as to be adapted to receive the implants of the present invention. It is also understood that implantation space preparation commonly leaves residual disc material D prior to implant placement.

FIG. 3 shows the implantation space 100, which has been prepared by partial disc and soft tissue removal adjacent to the vertebral body V. The preparation in FIG. 3 is shown as a posterior lumbar surgical approach, and the opening O into the disc space from the posterior is shown. The opening O may also be an opening prepared for transforaminal or oblique surgical approaches. Residual portions P of the vertebral pedicles are also shown.

Figure 4:
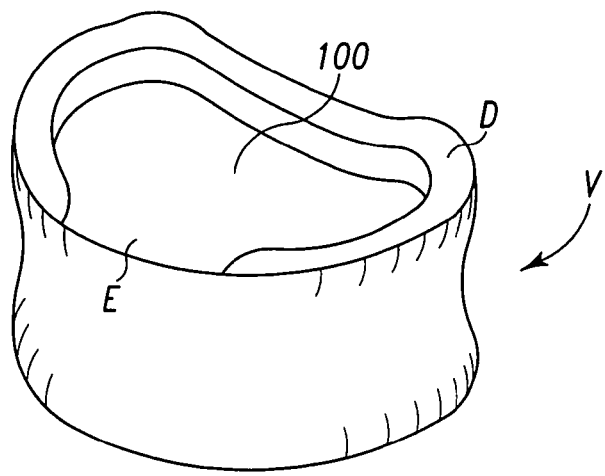
FIG. 4 is a perspective view of an implantation space formed through an anterior approach.

FIG. 4 shows the implantation space 100, which has been prepared by partial disc and soft tissue removal adjacent to the vertebral body V. The preparation in FIG. 4 is shown as an anterior surgical approach and the entrance E into the disc space from the anterior is shown. This representation can reflect a cervical, thoracic, or lumbar spinal intervertebral space preparation.

Figure 5:
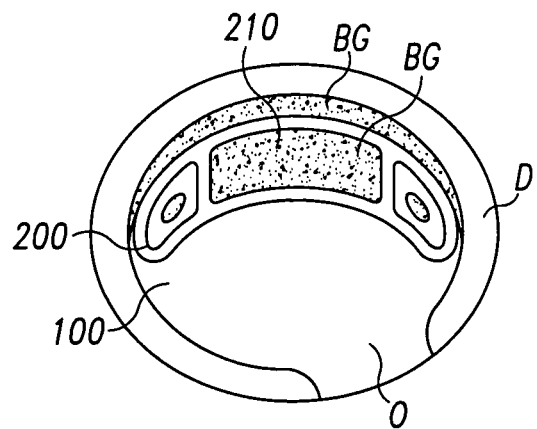
FIG. 5 is a top plan view of a vertebral body in the lumbar spine with an embodiment of an implant positioned in the implantation space of FIG. 2.

FIG. 5 shows a unilateral implant 200 seated in the implantation space 100 in accordance with an embodiment of the present invention. Bone graft material BG is shown anterior to the unilateral implant 200, as well as within a central void 210 of the unilateral implant 200.

Figure 6:
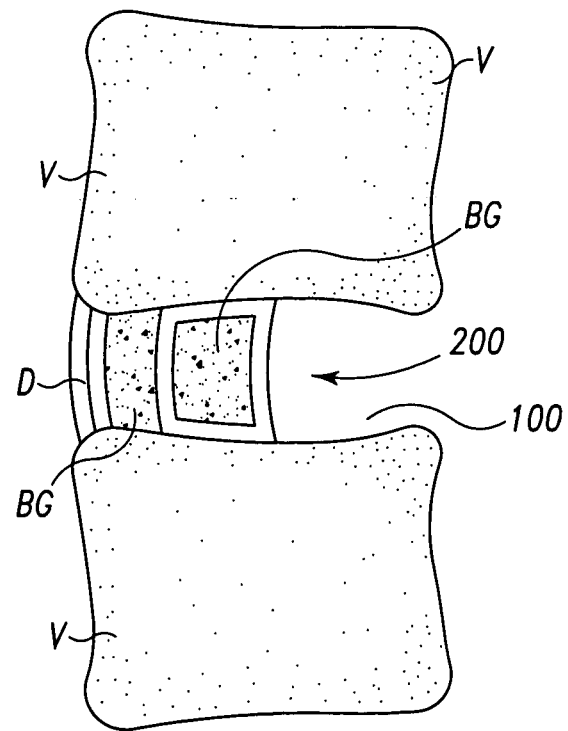
FIG. 6 is a side view of two adjacent vertebral bodies with the implant of FIG. 5 positioned in the implantation space of FIG. 2 through a posterior approach.

FIG. 6 shows a unilateral implant 200 seated in the implantation space 100. Bone graft material BG is shown anterior to the unilateral implant 200 but posterior to remaining disc D, as well as within the central void 210 of the unilateral implant 200.

Figure 7:
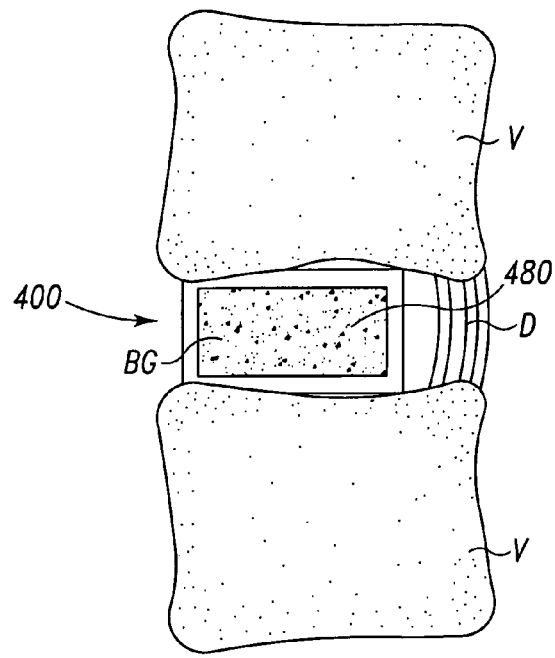
FIG. 7 is a side view of two adjacent vertebral bodies with an implant positioned in the implantation space of FIG. 2 through an anterior approach.

FIG. 7 shows an anterior implant 400 seated in the implantation space 100. Bone graft material BG is shown within a cavity 480 of the anterior implant 400.

Figure 8:
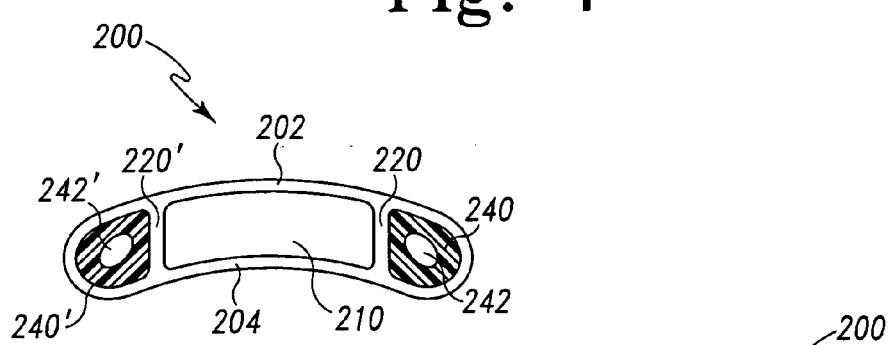
FIG. 8 is a top plan view of the implant of FIG. 5

FIG. 8 shows the unilateral implant 200 with an anterior aspect 202 and a posterior aspect 204. The central void 210 is shown. Traversing support structures 220, 220' extend from anterior 202 to posterior 204 aspects of the implant. In the lateral aspects of the unilateral implant 200 radiolucent blocks 240, 240' are shown, each with a central cavity 242, 242'.

Figure 9:
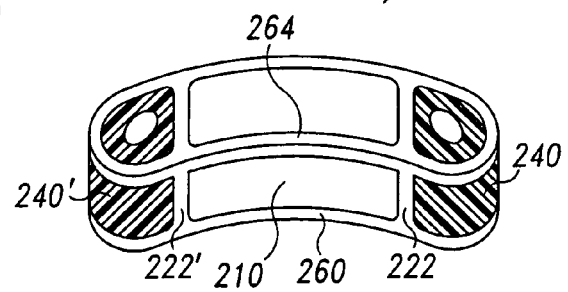
FIG. 9 is a rear perspective view of the implant of FIG. 5.

FIG. 9 shows the unilateral implant 200 as described in FIG. 8. The view from a posterior perspective shows the central void 210, the radiolucent blocks 240, 240' and posterior support columns 222, 222' which extend from an inferior aspect 260 to a superior aspect 264 of the implant.

Figure 10:
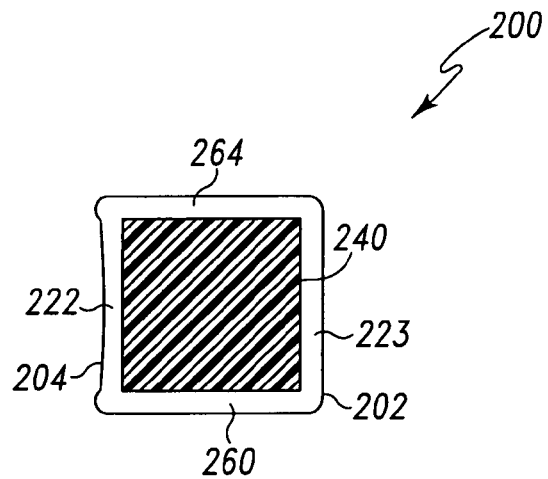
FIG. 10 is a side view of the implant of FIG. 5.

FIG. 10 shows the unilateral implant 200 as described in FIG. 8 from a lateral view. The radiolucent block 240 is shown positioned between the superior aspect 264 and the inferior aspect 260 of the implant. A posterior support column 222 and an anterior support column 223 between the superior aspect 264 and inferior aspect 260 are shown. In a lateral projection, anterior 202 and posterior 204 aspects to the implant are noted.

Figure 11:
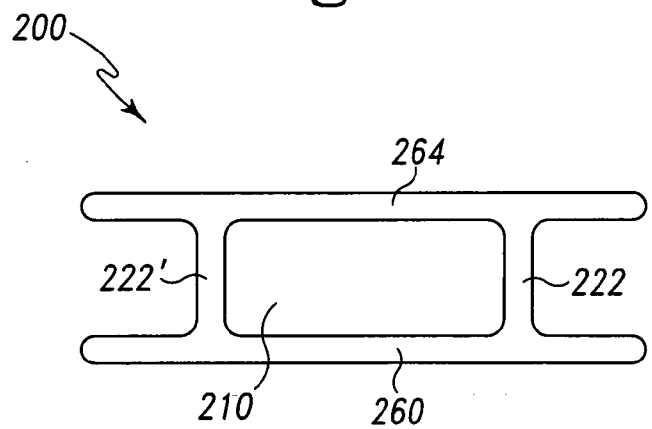
FIG. 11 is a rear view of the implant of FIG. 5.

FIG. 11 shows a posterior view of the implant as described in FIGS. 8 and 9 without appearance of the radiolucent blocks 240, 240', in order to show radiographic appearance. Only the posterior support columns 222, 222' extending between the inferior aspect 260 and the superior aspect 264 of the implant are visualized radiographically due to the selected radio-opaque nature of the material implemented in this embodiment. Anterior support columns 223, 223' are hidden behind posterior support columns 222, 222' when the unilateral implant 200 is visualized radiographically directly from the posterior.

Figure 12:
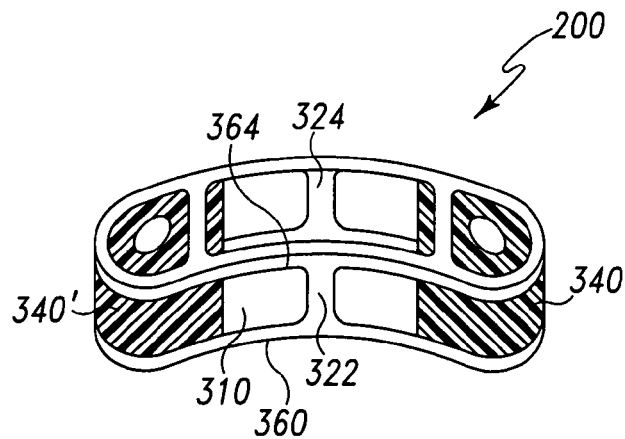
FIG. 12 is a rear perspective view of another embodiment of an implant for use in the implantation space of FIG. 2.

FIG. 12 shows another embodiment of the invention with a center-support implant 300 in rear perspective view. A central volume 310, and radiolucent lateral blocks 340, 340', as well as anterior support structure 324, and posterior support structure 322 are noted.

Figure 13:
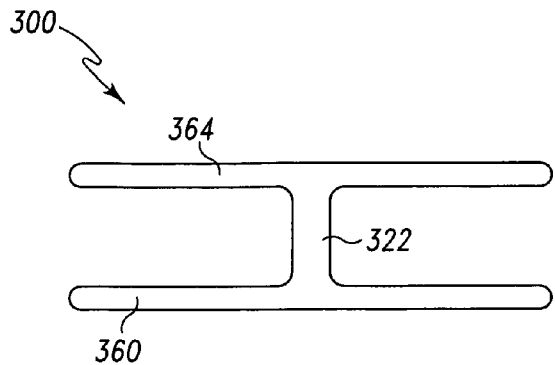
FIG. 13 is a rear view of the implant of FIG. 12.

FIG. 13 shows a posterior view of the implant as described in FIG. 12 without appearance of the radiolucent lateral blocks 340, 340' in order to show radiographic appearance. Only the posterior support structure 322, which overlaps in this view the anterior support structure 324, seen in FIG. 12, is visualized radiographically between the inferior portion 360 and the superior portion 364 of the implant due to the selected radio-opaque nature of the material implemented in this embodiment.

Figure 14:
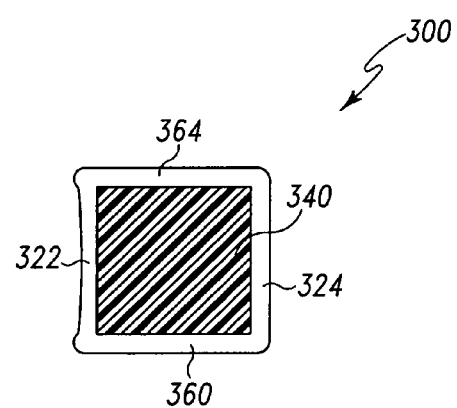
FIG. 14 is a side view of the implant of FIG. 12.

FIG. 14 shows the center-support implant 300 as described in FIG. 12 from a lateral view. The radiolucent lateral block 340 is shown positioned between the superior portion 364 and the inferior portion 360 of the implant. In this lateral projection the anterior support structure 324 and posterior support structure 322 of the implant are noted.

Figure 15:
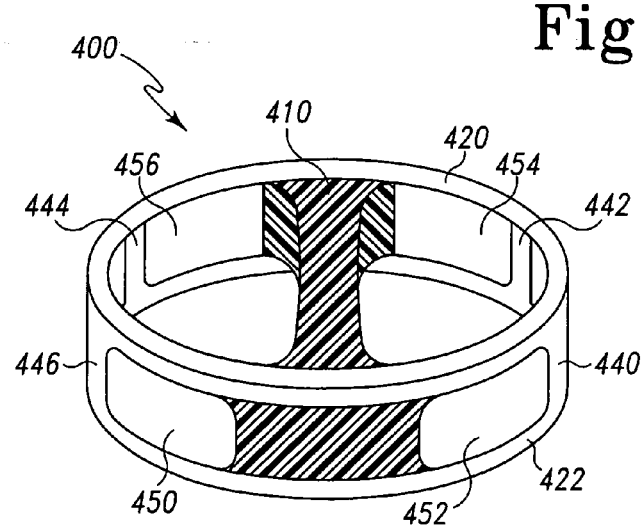
FIG. 15 is a rear perspective view of an embodiment of an implant suited for anterior placement into a cervical or lumbar intervertebral disc space.

FIG. 15 illustrates an anterior implant 400. In some embodiments, the anterior implant 400 may be placed through an anterior surgical approach. However, the anterior implant 400 may also be placed by other surgical approaches such as, but not limited to, an anterior-oblique approach or a lateral approach. A large central strut 410 made of radiolucent material is shown traversing the implant. Upper rim 420 and lower rim 422 are attached to the central strut 410 and further supported and connected to one another through supportive structures 440, 442, 444, 446. Openings through the sides of the implant are noted 450, 452, 454, 456. These openings may permit for the growth of bone through and into anterior implant 400, though the invention is not so limited.

Figure 16:
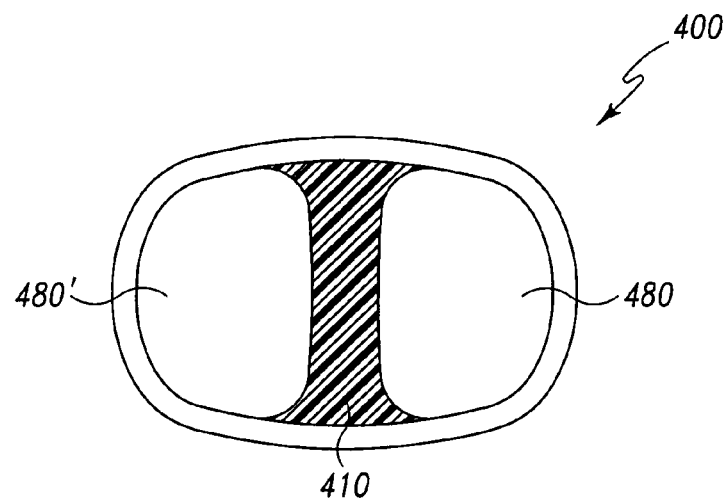
FIG. 16 is a top plan view of the implant of FIG. 15.

FIG. 16 shows a top plan view of the anterior implant 400 as described in FIG. 15. The large central strut 410 is noted. Two cavities 480, 480' within the anterior implant 400 are shown on either side of the strut 410. These cavities may permit for the growth of bone through and into anterior implant 400, though the invention is not so limited.

Figure 17:
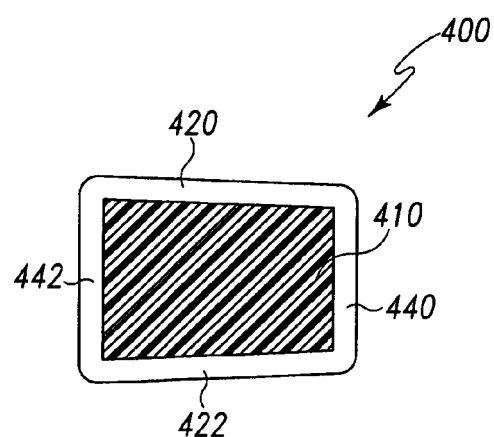
FIG. 17 is a side view of the implant of FIG. 15.

FIG. 17 shows a lateral view of the anterior implant 400 as described in FIGS. 15 and 16. Upper rim 420 and lower rim 422 are shown, as is the lateral view of the central strut 410. Given the radiolucent nature of the central strut 410, on radiographic visualization only the upper rim 420 and lower rim 422 as well as radio-opaque supportive structures 440, 442 would be noted. The remaining two supportive structures 444, 446 noted in FIG. 15 are obscured in a lateral view by the supportive structures 440, 442. Further, angulation between the upper rim 420 and lower rim 422 may facilitate insertion of anterior implant 400 between the two adjacent vertebral bodies and permit control of sagittal plane intervertebral alignment.

Figure 18:
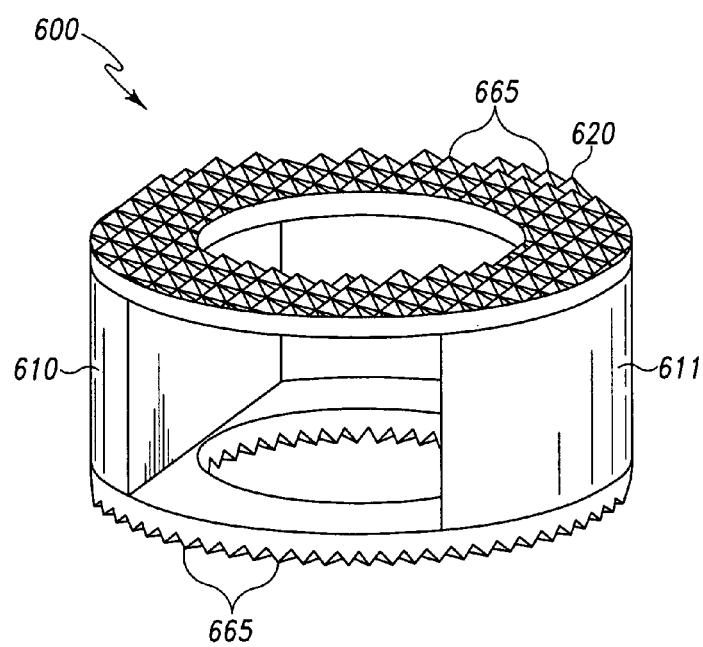
FIG. 18 is perspective view of an embodiment of the implant.

FIG. 18 illustrates another embodiment of an implant designed primarily for implantation from an anterior surgical approach. The open anterior implant 600 illustrates an implant having a generally rounded exterior shape for promoting fusion between an inferior vertebral body and a superior vertebral body. Many generally rounded shapes are contemplated under the invention. By way of example and without limitation, the exterior shape may be round, oval, the shape of the cortical rim of a vertebral body, the general shape of the cross-section of a kidney, or the general shape of a racetrack having straight sides connecting substantially rounded ends.

A first rim 620 is shown around a periphery of the open anterior implant 600, the first rim 620 has a detectable radiographic signature. The term radiographic signature as used herein refers to a resulting visualization on radiographic devices. A radiolucent block, for example, is faintly to indistinguishably visible on a radiograph, and would therefore be considered to have less of a radiographic signature than a radio-opaque metal such as titanium.

The illustrated first rim 620 has a substantially uniform width. In other embodiments, the width of the first rim 620 may vary to improve engagement with other portions of the implant or cooperating implants, or may vary to accomplish better anatomical fit. The first rim 620 shown is continuous about the periphery. Some embodiments include a rim that only extends between select portions of the periphery of the implant.

The first rim 620 illustrated in FIG. 18 includes protrusions 665 configured to face an adjacent vertebral body and engage the vertebral body. In embodiments where the first rim 620 is made from a metallic material, an advantage may be established in forming protrusions 665. Metal teeth, protrusions, and other surface characteristics may be both stronger and capable of being more effectively sharpened to better engage bone surfaces. In some embodiments, the first rim 620 is made from titanium, a biocompatible, radio-opaque metal.

FIG. 18 also illustrates a member embodied in a first segment 610 and coupled to the first rim 620. The first segment 610 has less of a radiographic signature than the first rim 620 in some embodiments. The first segment 610 may be made from a radiolucent material such as PEEK or any other biocompatible material that is less radiographically visible than the material of the first rim 620. As shown, the first segment 610 added to the first rim 620 increases the height of the spacing provided by the open anterior implant 600.

Figure 20:
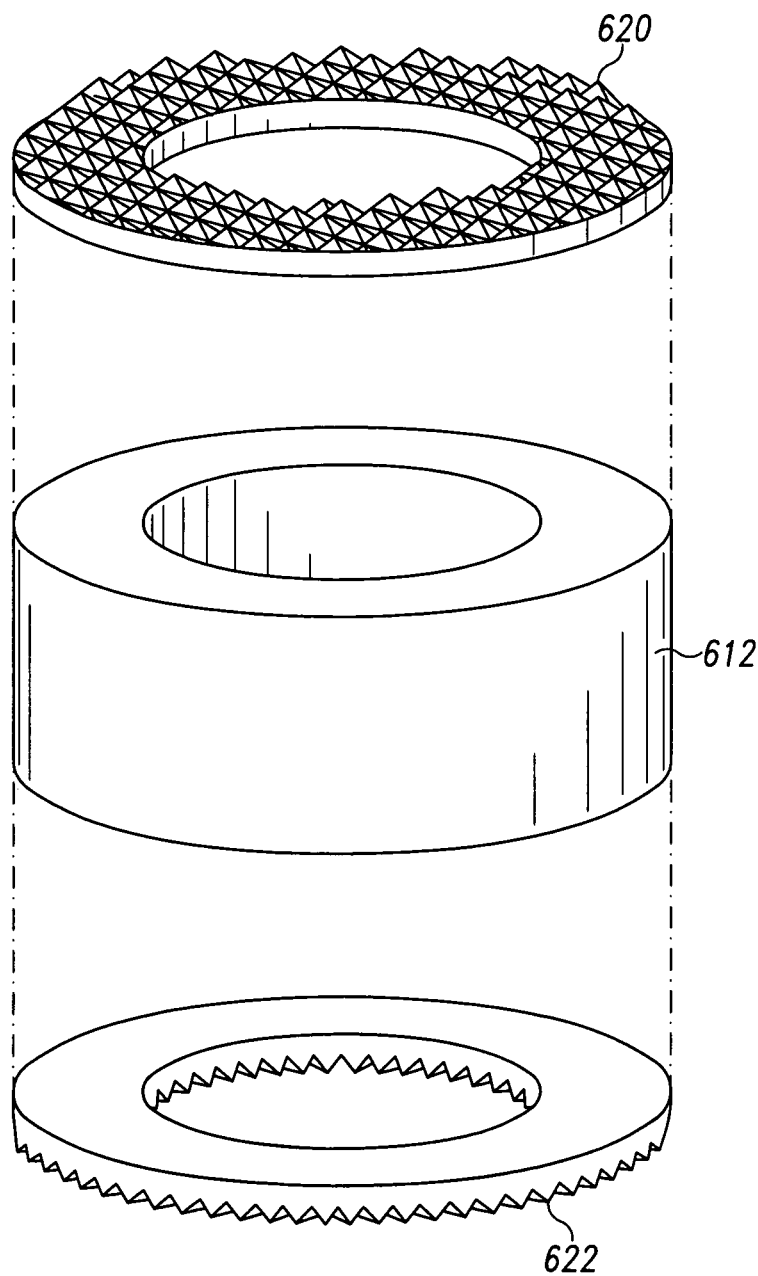
FIG. 20 is an exploded perspective view of an embodiment of the implant

Another member embodiment of the invention is illustrated in FIG. 20 and includes tubular member 612. The tubular member 612 is continuous about the periphery of the implant. The tubular member 612 may also be mated with the first rim 620.

Figure 19:
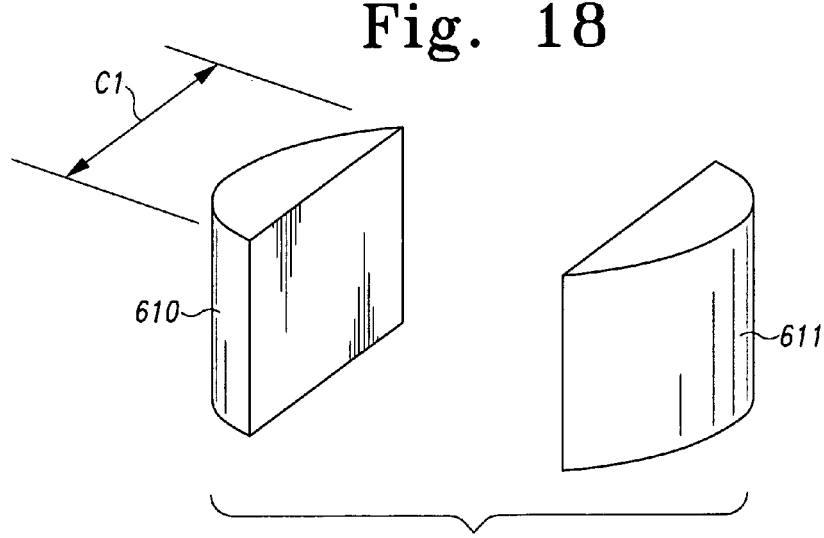
FIG. 19 is a view of selected components of the implant of FIG. 18.

The first segment 610 illustrated in FIGS. 18 and 19 has a chord length C1. The cord length C1 of embodiments of the invention is less than ninety percent of the length of an outer average diameter of the first rim 620. In some more specific embodiments, the cord length C1 is less than two-thirds of the length of an outer average diameter of the first rim 620. FIGS. 18 and 19 also illustrate an second segment 611 which is generally on the opposite side of the open anterior implant 600 from the first segment 610.

In some embodiments, the first segment 610 is configured for positioning on an anterior side of an implant. In other embodiments, the first segment 610 is configured for positioning on a posterior side of an implant. In still other embodiments, the first segment 610 is configured for positioning on a lateral side of an implant. The second segment 611 may be configured for placement adjacent to or opposite from the first segment 610 in conjunction with any placement of the first segment 610.

FIGS. 18 and 20 illustrate a second rim configured to couple to the first and second segments 610, 611 and the tubular member 612 respectively. The second rim 622 may be coupled around a periphery of the open anterior implant 600, the second rim 622 has a detectable radiographic signature. The illustrated second rim 622 has a substantially uniform width. In other embodiments, the width of the second rim 622 may vary to improve engagement with other portions of the implant or cooperating implants, or may vary to accomplish better anatomical fit. The second rim 622 shown is continuous about the periphery.

The second rim 622 illustrated in FIG. 18 includes protrusions 665 configured to face an adjacent vertebral body and engage the vertebral body. In embodiments where the second rim 622 is made from a metallic material, an advantage may be established in forming protrusions 665. Metal teeth, protrusions, and other surface characteristics may be both stronger and capable of being more effectively sharpened to better engage bone surfaces. In some embodiments, the second rim 622 is made from titanium, a biocompatible, radio-opaque metal.

As shown in FIGS. 18 and 20, the first and second segments 610, 611 and the tubular member 612 respectively are illustrated as approximately the same anterior, posterior, and lateral size as the first and second rims 620, 622. However, in some embodiments, the first and second segments 610, 611 and the tubular member 612 extend beyond the extents of the first and second rims 620, 622 and may encapsulate at least portions of the first and second rims 620, 622.

In some embodiments, implants of multiple sizes and configurations may be formed by assembling two or more of various, cooperating rims, supports, and members. An embodiment of the invention may include a kit of variously sized rims, supports, and members that are intended to be assembled by surgeons, product resellers, other users, and distributors.

Members such as, but not limited to, the first and second segments 610, 611 and the tubular member 612 may also be made at least in part of material with a lower modulus of elasticity than the rims or supports. In some circumstances, it may be desirable to provide a modulus of elasticity that more nearly approximates the modulus of elasticity of bone, or that at least reduces the rigidity of the implant somewhat.

FIGS. 21A-25C are simplified graphical representations of various configurations of implant embodiments of the invention. FIG. 21A is a plan view consistent with an axial radiographic image. FIG. 21B is a side view consistent with a lateral radiographic image. FIG. 21C is a posterior view consistent with a posterior to anterior radiographic image.

Each implant depicted in FIGS. 21A-25C will be represented by a superior rim 20, an inferior rim 22, posterior supports 40, 46, anterior supports 44, 42, and lateral supports 25, 26 where appropriate. Each of the supports is represented here as a cylindrical component. However, each may be of any desired configuration, such as but not limited to, rectangular, square, circular, oval, polygonal, or variable in cross-section along its length. Less radiographic or radiolucent members such as the central strut 410, first segment 610, second segment 611 and the tubular member 612, as have been disclosed above, are not shown in FIGS. 21A-25C, but any size or configuration of such members is contemplated for each of the implants represented. Although angulation for lordotic and kyphotic correction is not illustrated in FIGS. 21A-25C, such angulation is contemplated for each embodiment.

FIGS. 21A-23C and 25A-25C will further illustrate relationships between relative alignments among two or more of the supports, as viewed radiographically from at least one of the anterior, posterior, and lateral sides, and rotational position of the implant about a vertical axis. A vertical axis for the purpose of this orientation is considered vertical as viewed in the posterior views illustrated.

FIGS. 21A-21C illustrate supports 40, 46 in the posterior half of the implant that are configured to block radiographic visualization of supports 42, 44 in the anterior half of the implant when the implant is radiographically viewed from a posterior side of the implant. FIGS. 21A-21C also illustrate a support 40 in the posterior half of the implant configured to block radiographic visualization of a support 46 on the contralateral side of the implant when the implant is radiographically viewed from a lateral side of the implant; and a support 42 in the anterior half of the implant are configured to block radiographic visualization of a support 44 on the contralateral side of the implant when the implant is radiographically viewed from a lateral side of the implant.

FIGS. 22A-22C show a support 25 in the posterior half of the implant configured to block radiographic visualization of a support 26 on the contralateral side of the implant when the implant is radiographically viewed from a lateral side of the implant. As used herein, the posterior half will include a centerline between the anterior and posterior halves. As shown in FIG. 22C, when the implant is viewed radiographically from a posterior side, the lateral space between supports 25, 26 indicates the rotational position of the implant. Additionally, the alignment of the supports 25, 26 with ends of the superior rim 20 when viewed from a posterior side indicates rotational position of the implant.

FIGS. 23A-23C illustrate a support 40 in the posterior half of the implant configured to block radiographic visualization of a support 42 in the anterior half of the implant when the implant is radiographically viewed from a posterior side of the implant. When the implant is viewed radiographically from a lateral side, the anterior to posterior spaces between the support 40 in the posterior half of the implant and the support 42 in the anterior half of the implant indicates the rotational position of the implant. Additionally, the alignment of the supports 40, 42 with ends of the superior rim 20 when viewed from a lateral side indicates rotational position of the implant.

FIGS. 24A-24C illustrate an implant with a superior rim 20 and an inferior rim 22 that are coupled to one another by one or more less radiographically detectable or radiolucent members.

FIGS. 25A-25C illustrate and implant where, when the implant is viewed radiographically from a posterior side, lateral spaces S1, S2 between the support 40 in the posterior half of the implant and the supports 42, 44 in the anterior half of the implant are substantially equidistant. FIGS. 25A-25C also illustrate a support 42 in the anterior half of the implant configured to block radiographic visualization of a support 44 on the contralateral side of the implant when the implant is radiographically viewed from a lateral side of the implant.

While the implants are intended primarily for use in spinal fusion, it is appreciated that they may be modified or adapted to receive fusion promoting substances and/or materials within them such as, but not limited to cancellous bone, bone derived products, chemotherapeutic agents, antimicrobial agents, or others. In some embodiments, the implants consists of materials such as, but not limited to, titanium and its alloys, ASTM material, cobalt chrome, tantalum, ceramic, poly-ether-ether-ketone (PEEK), various plastics, plastic composites, carbon fiber composites, coral, and can include artificial materials which are at least in part bioresorbable. The radiographic appearance of the structural materials employed in the implants are intended to be of varying nature such that optimal visualization of implant placement, implant-bone interfaces and/or bone ingrowth and through-growth can be achieved.

While the descriptions reveal various relationships, parallel or not, of upper to lower surfaces of the implants, it should be noted that deliberate angulation between surfaces relative to each other is possible. Subsequently, when implanted into the spine, such implants permit position of the adjacent vertebral bodies in angular relationship to each other to restore the natural curvature of the spine, such as lordosis for example. It should also be noted that significant variations in shape of the implants are possible including but not limited to: kidney shaped, rounded, wedge shaped, cylindrical, trapezoidal, rectangular, oblong, and oval.

Outer surfaces may contain threading or particular unevenness for improved insertion or anchorage into surrounding tissues or bone. In any of the embodiments of the present invention, the implants may include, be made of, treated, coated, filled, used in combination with, or have a hollow space or opening for containing artificial or naturally occurring materials and/or substances suitable for implantation in the human spine. These materials, and/or substances, may include any source of osteogenesis, bone growth promoting materials, bone, bone derived substances or products, demineralized bone matrix, mineralizing proteins, ossifying proteins, bone morphogenetic proteins, hydroxyapatite, genes coding for the production of bone, and bone including, but not limited to, cortical bone, antibiotics, cancer treating substances, infection treating substances or other disease treating substances. The implant can include, at least in part materials that are bioabsorbable and/or resorbable in the body. The implants of the present invention can be formed of a porous material or can be formed of a material that intrinsically participates in the growth of bone between adjacent vertebral. At least a portion of the implant may be treated to promote bone ingrowth between the implant and the adjacent vertebral bodies.

The implant of the present invention may be used in combination with a spinal fixation device such as any device, regardless of material, that can be inserted into any portion of the spine, such as but not limited to interbody spinal implants, structural bone grafts, mesh, cages, spacers, staples, bone screws, plates, rods, tethers of synthetic material or wires, or other spinal fixation instrumentation. While the invention has been described with reference to particular embodiments, it will be appreciated by those of ordinary skill in the art that various modifications can be made to the invention itself without departing from the spirit and scope thereof. All changes and modifications that are within the spirit of the invention are hereby anticipated and claimed.

A method under the invention includes implanting an intervertebral implant from an anterior surgical approach. An implant comprising the following is provided: a first rim around a periphery of the implant, the first rim having a detectable radiographic signature, and a member coupled to the first rim, the member having less of a radiographic signature than the first rim. The member adds vertebral spacing height to the first rim. Other implants with compatible radiographic characteristics are also contemplated for use under embodiments of the method.

The method further includes radiographically observing placement of the implant between superior and inferior vertebral bodies. This observation may be accomplished by capturing radiographic images along one or more of an anterior to posterior radiographic view and a lateral radiographic view. Such radiographic viewing in some embodiments includes viewing from any lateral direction and is not limited to direct posterior, anterior, and lateral directly, but includes oblique departures from these directions. Effective radiographic viewing is enabled by embodiments of the invention that provide medial-lateral and anterior-posterior viewing paths. However, selective placement of radio-opaque materials that both structurally support and notify a surgeon of implant orientation are present in some embodiments of the invention in combination with these viewing paths.

Radiographically observing placement of the implant may include observing relative alignment of two or more supports extending between the superior and inferior portions of the implant. By observing relative alignment of two or more supports coupled to the first rim, orientation of the implant may be determined.

The method may also include radiographically observing bone growth between the superior and inferior vertebral bodies by capturing radiographic images along one or more of an anterior to posterior radiographic view and a lateral radiographic view. Such radiographic viewing in some embodiments includes viewing from any lateral direction and is not limited to direct posterior, anterior, and lateral, but includes oblique departures from these directions. Observation of bone growth is enhanced by the provision of viewing paths provided through an implant that only include bone growth volumes and radiolucent materials.

A method of assembling an intervertebral implant includes providing an implant with a first rim around a periphery of the implant, the first rim having a detectable radiographic signature, a support coupled to the first rim, the support having a detectable radiographic signature, and a second rim coupled to the support, the second rim having a detectable radiographic signature.

Embodiments of the method include applying a member between the first rim and the second rim. The member of the embodiment having less of a radiographic signature than the first rim. By way of example, the member may be a radiolucent material, such as PEEK. As illustrated herein, the member may include one or more of a central strut 410, a first segment 610, a second segment 611, or a tubular member 612.

Applying the member may be accomplished in various ways. The distal end may be formed around at least a portion of one of the first rim, the second rim, and the support. To accomplish this, the material of the member may be cast, injected, or molded directly around at least a portion of one of the first rim, the second rim, and the support. The body may be included as a part of a mold or cast, or encapsulated within a mold or cast for application to a portion of one of the first rim, the second rim, and the support.

Applying the member may also include interconnecting a material with at least a portion of at least one of the first rim, the second rim, and the support. Interconnecting may also include casting, injecting, or molding material, but without encapsulating a portion of at least one of the first rim, the second rim, and the support. Interconnecting material may also involve forming a member completely separately from the first rim, the second rim, and the support by milling, casting, forming, injecting, or molding. After the member is formed, it may then be applied to the body by any method of adhesion, interdigitation, or interconnection. In some embodiments, interconnecting may be accomplished by snapping the material of the member to, between, or among the first rim, the second rim, and the support.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. An intervertebral implant comprising:
   a body having a generally rounded exterior shape for promoting fusion between an inferior vertebral body and a superior vertebral body, wherein the body comprises:
   a generally rounded first rim defining a periphery of the implant and including a central aperture, an upper surface configured to face one of the inferior vertebral body and the superior vertebral body and a lower surface opposite the upper surface, the first rim having a detectable radiographic signature; and
   a member comprising a top surface coupled directly to the lower surface of the first rim, the member being made from a first material having less of a radiographic signature than the first rim, the member having a generally half-moon shaped cross-sectional configuration and being coupled directly to the first rim in a manner such that the member does not obstruct a passageway defined by the central aperture,
   wherein the member includes an anterior support and a posterior support, the supports each having a radiographic signature greater than that of the first material, the supports being positioned such that the posterior support blocks radiographic visualization of the anterior support when the implant is radiographically viewed from a posterior side of the implant,
   wherein the member adds vertebral spacing height to the first rim.

2. The intervertebral implant of claim 1 wherein the generally rounded exterior shape is at least one of round, oval, vertebral body cortical rim shaped, kidney shaped, and racetrack shaped.

3. The intervertebral implant of claim 1 wherein the first rim is a substantially uniform width.

4. The intervertebral implant of claim 1 wherein the first rim is continuous about the periphery.

5. The intervertebral implant of claim 1 wherein the first rim contains protrusions facing an adjacent vertebral body to engage the vertebral body.

6. The intervertebral implant of claim 1 wherein the first rim is made of a biocompatible metal.

7. The intervertebral implant of claim 6 wherein the first rim is made of titanium.

8. The intervertebral implant of claim 1 wherein the member is made from a radiolucent material.

9. The intervertebral implant of claim 1 wherein the member is a first segment with a chord length less than ninety percent of an outer average diameter of the first rim.

10. The intervertebral implant of claim 9 wherein the member is a first segment with a chord length less than two-thirds of an outer average diameter of the first rim.

11. The intervertebral implant of claim 9 further comprising a second segment generally opposite from the first segment.

12. The intervertebral implant of claim 11 wherein the first segment is positioned on an anterior side of the implant and the second segment is positioned on a posterior side of the implant.

13. The intervertebral implant of claim 9 wherein the first segment is positioned on an anterior side of the implant.

14. The intervertebral implant of claim 9 wherein the first segment is positioned on a posterior side of the implant.

15. The intervertebral implant of claim 9 wherein the first segment is positioned on a lateral side of the implant.

16. The intervertebral implant of claim 1 further comprising a second rim coupled to the member in a generally opposite position from the first rim.

17. The intervertebral implant of claim 1 wherein an anterior portion of the implant is taller than a posterior portion of the implant to assist in restoring lordotic curvature between the inferior and superior vertebral bodies.

18. The intervertebral implant of claim 1 wherein the first rim comprises a uniform thickness defined by a distance between the upper and lower surfaces and the lower surface is free of any projections.

19. The intervertebral implant of claim 1 wherein the lower surface and the top surface are entirely planar.

20. The intervertebral implant of claim 1 wherein the lower surface of the first rim is planar between a first end of the first rim and an opposite second end of the first rim, and is planar between a third end of the first rim that is positioned perpendicular to the first and second ends and a fourth end opposite the third end.

21. The intervertebral implant of claim 1 wherein the member has a solid configuration that is free of any gaps or openings.

22. The intervertebral implant of claim 1 wherein the first rim comprises an outer surface between the upper and lower surfaces of the first rim, each portion of the outer surface being equidistant from a center of the central aperture.

23. The intervertebral implant of claim 1 wherein the central opening has a continuous radius of curvature.

24. The intervertebral implant of claim 1 further comprising a second member generally opposite from the member, the second member comprising a top surface coupled directly to the lower surface of the first rim, the second member having a generally half-moon shaped cross-sectional configuration and being coupled directly to the first rim in a manner such that the member does not obstruct the passageway defined by the central aperture, the member and the second member each including planar sidewalls that face one another.

25. The intervertebral implant of claim 24, wherein the sidewalls of the member and the second member are free of any gaps or openings.

26. The intervertebral implant of claim 1 wherein the first rim defines a first axis that bisects the first rim in a first direction and a second axis extending perpendicular to the first axis that bisects the first rim in a second direction, the first and second axes intersecting at a center of the central aperture.

27. An intervertebral implant, comprising:
a body having a generally rounded exterior shape for promoting fusion between an inferior vertebral body and a superior vertebral body, wherein the body comprises:
a generally rounded first rim defining an upper periphery of the implant and including a first central aperture, an upper surface configured to face one of the inferior vertebral body and the superior vertebral body and a lower surface opposite the upper surface, the first rim having a detectable radiographic signature;
a generally rounded second rim defining a lower periphery of the implant and including a second central aperture, a lower surface configured to face the other of the inferior vertebral body and the superior vertebral body and a planar upper surface, the second rim having the same said detectable radiographic signature;
a first member having about a half-moon shaped cross-sectional configuration along a vertical axis thereof, the first member comprising a first end surface coupled directly to the lower surface of the first rim and a second end surface coupled directly to the upper surface of the second rim, the first member being positioned about a periphery of the first and second rims such that the first member does not obstruct a passageway defined between the first and second central apertures, the first member being made from a first material having less of a radiographic signature than the first and second rims;
a second member opposing said first member having about a half-moon shaped cross-sectional configuration along a vertical axis thereof, the second member comprising a third end surface coupled directly to the lower surface of the first rim and a fourth end surface coupled directly to the upper surface of the second rim, the second member being positioned about a periphery of the first and second rims such that the second member does not obstruct the passageway defined between the first and second central apertures, the second member being made from the first material,
wherein the first and second member each include an anterior support and a posterior support, the supports each having a radiographic signature greater than that of the first material, the supports being positioned such that the posterior supports block radiographic visualizations of the anterior supports when the implant is radiographically viewed from a posterior side of the implant,
wherein the first and second members add vertebral spacing to the first and second rims.

28. The intervertebral implant of claim 27, wherein the first rim includes a plurality of first protrusions covering an entire upper surface of the first rim and the second rim includes a plurality of second protrusions covering an entire lower surface of the second rim.

29. The intervertebral implant of claim 27, wherein the first and second members have a chord length less than ninety percent of an outer average diameter of the first rim.

30. The intervertebral implant of claim 29, wherein the first and second members have a chord length less than two-thirds of an outer average diameter of the first rim.

* * * * *